(12) United States Patent
Abe et al.

(10) Patent No.: US 8,742,032 B2
(45) Date of Patent: Jun. 3, 2014

(54) MEDICAL APPLIANCE HAVING A SLIDABLE COATING LAYER AND SYRINGE

(71) Applicant: Terumo Kabushiki Kaisha, Shibuya-ku (JP)

(72) Inventors: Yoshihiko Abe, Kanagawa (JP); Eiji Watanabe, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 70 days.

(21) Appl. No.: 13/628,833

(22) Filed: Sep. 27, 2012

(65) Prior Publication Data

US 2013/0030380 A1 Jan. 31, 2013

Related U.S. Application Data

(63) Continuation of application No. PCT/JP2011/057679, filed on Mar. 28, 2011.

(30) Foreign Application Priority Data

Mar. 30, 2010 (JP) ................................ 2010-076814

(51) Int. Cl.
| | |
|---|---|
| *C08G 77/12* | (2006.01) |
| *C08G 77/20* | (2006.01) |
| *A61L 31/10* | (2006.01) |
| *A61M 5/31* | (2006.01) |
| *A61M 5/315* | (2006.01) |
| *A61L 29/08* | (2006.01) |

(52) U.S. Cl.
USPC ............ 525/477; 604/221; 604/265; 604/187

(58) Field of Classification Search
None
See application file for complete search history.

(56) References Cited

U.S. PATENT DOCUMENTS 4,631,321 A 12/1986 Suzuki
5,290,228 A * 3/1994 Uemura et al. ................. 604/90
(Continued)

FOREIGN PATENT DOCUMENTS

EP 0 953 675 A2 11/1999
EP 2 226 088 A1 9/2010
(Continued)

OTHER PUBLICATIONS

Notification of Transmittal Translation of the International Preliminary Report on Patentability (Forms PCT/IB/338 and PCT/IB/373) and the Written Opinion of the International Searching Authority (Form PCT/ISA/237) dated Nov. 22, 2012, issued in corresponding International Application no. PCT/JP2011/057679. (6 pages).

(Continued)

*Primary Examiner* — Robert S Loewe
(74) *Attorney, Agent, or Firm* — Buchanan Ingersoll & Rooney PC

(57) ABSTRACT

A medical appliance having a slidable coating layer that moves in contact with an inner surface of a medical member or that of a lumen and has the slidable coating layer formed at a part thereof which contacts the medical member or the lumen. The slidable coating layer is formed of a composition which does not contain solid fine particles and contains a silicone-based resin which is a product of an addition reaction between silicone having a vinyl group and silicone having a hydrogen group bonded to a silicon atom.

23 Claims, 4 Drawing Sheets

(56) References Cited

U.S. PATENT DOCUMENTS

| | | | |
|---|---|---|---|
| 5,352,378 A * | 10/1994 | Mathisen et al. | 508/215 |
| 6,200,627 B1 * | 3/2001 | Lubrecht | 427/2.28 |
| 6,200,915 B1 | 3/2001 | Adams et al. | |
| 6,746,430 B2 * | 6/2004 | Lubrecht | 604/230 |
| 7,111,848 B2 | 9/2006 | Tachikawa et al. | |
| 7,332,227 B2 * | 2/2008 | Hardman et al. | 428/447 |
| 7,648,487 B2 * | 1/2010 | Ito et al. | 604/230 |
| 2003/0096904 A1 | 5/2003 | Hakuta et al. | |
| 2004/0084852 A1 | 5/2004 | Tachikawa et al. | |
| 2004/0209784 A1 | 10/2004 | Hardman et al. | |
| 2006/0200084 A1 * | 9/2006 | Ito et al. | 604/230 |
| 2007/0299402 A1 | 12/2007 | Ishii et al. | |
| 2010/0069523 A1 | 3/2010 | Alvarez et al. | |
| 2010/0076158 A1 | 3/2010 | Imoto et al. | |
| 2010/0324501 A1 | 12/2010 | Horiuchi et al. | |
| 2011/0097579 A1 | 4/2011 | Mizuno et al. | |
| 2011/0236458 A1 | 9/2011 | Farrar et al. | |

FOREIGN PATENT DOCUMENTS

| | | |
|---|---|---|
| JP | 60-181162 A | 9/1985 |
| JP | 62-32970 A | 2/1987 |
| JP | 06-183555 A | 7/1994 |
| JP | 07-138480 A | 5/1995 |
| JP | 11-350361 A | 12/1999 |
| JP | 2002-037947 A | 2/2002 |
| JP | 2002-089717 A | 3/2002 |
| JP | 2004-321614 A | 11/2004 |
| JP | 2006-167110 A | 6/2006 |
| JP | 2006-520241 A | 9/2006 |
| JP | 2008-000287 A | 1/2008 |
| JP | 2008-144024 A | 6/2008 |
| JP | 2009-051916 A | 3/2009 |
| JP | 2010-513664 A | 4/2010 |
| JP | 2010-535563 A | 11/2010 |
| WO | WO 2009/084646 A1 | 7/2009 |

OTHER PUBLICATIONS

International Search Report (Form PCT/ISA/210) issued on Jun. 19, 2012, by the Japanese Patent Office in International Application No. PCT/JP2012/057684. (5 pages).

Notification of Transmittal of Translation of the International Preliminary Report on Patentability (Forms PCT/IB/338 and PCT/IB/373) and the Written Opinion of the International Searching Authority (Form PCT/ISA/237) issued on Oct. 17, 2013, by the International Bureau of WIPO in International Application No. PCT/JP2012/057684. (10 pages).

Abe et al., U.S. Appl. No. 14/042,468, entitle "Medical Appliance Having a Slidable Coating Layer and Syringe" filed on Sep. 30, 2013.

International Search Report (PCT/ISA/210) issued on May 31, 2011, by the Japanese Patent Office as the International Searching Authority for International Application No. PCT/JP2011/057679.

\* cited by examiner

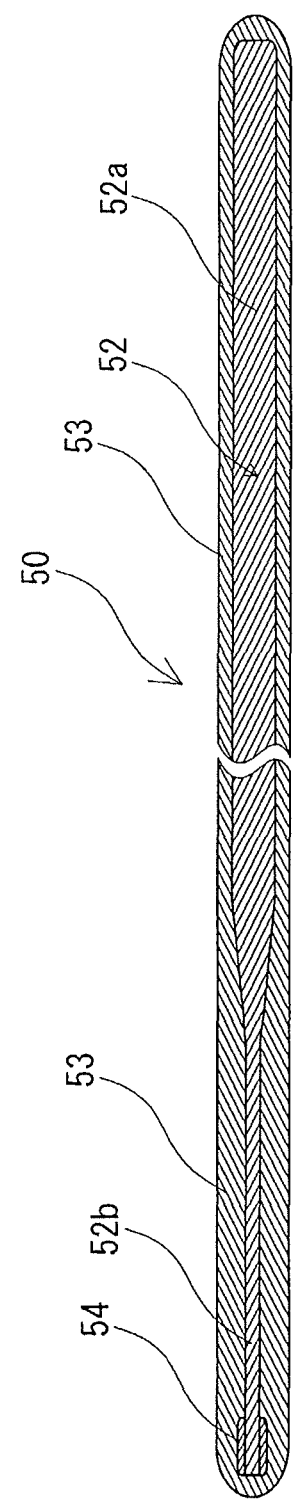

MEDICAL APPLIANCE HAVING A SLIDABLE COATING LAYER AND SYRINGE

CROSS REFERENCES TO RELATED APPLICATIONS

This application claims priority as a continuation application under 35 U.S.C. §120 to PCT/JP2011/057679, which was filed as an International Application on Mar. 28, 2011 designating the U.S., and which claims priority to Japanese Application No. 2010-076814 filed in Japan on Mar. 30, 2010. The entire contents of these applications are hereby incorporated by reference in their entireties.

TECHNICAL FIELD

Disclosed is a medical appliance with a slidable coating layer having a stable sliding performance, for example, a gasket for a syringe and the syringe having the gasket having a stable sliding performance.

BACKGROUND DISCUSSION

A prefilled syringe in which a medical agent solution is filled in advance can be used to limit or prevent use of a wrong medical agent, limit or prevent hospital infection, reduce waste, and increase efficiency in hospital service. Syringes including a syringe to be used as the prefilled syringe can be constructed of an outer cylinder, a gasket slidable inside the syringe, and a plunger for operating the movement of the gasket respectively. To enhance the sliding performance of the gasket and obtain a high degree of flow accuracy without generating a large irregularity in the discharge of the medical agent solution from the syringe, silicone oil or the like can be applied to a sliding portion of the outer surface of the gasket or the inner surface of the syringe as a lubricant. Depending on the kind of the medical agent solution, an interaction can occur between the medical agent solution and the lubricant such as the silicone oil. When the medical agent solution is stored for a long time after the medical agent solution is filled in the syringe, it can be modified by the interaction. Thus it can be difficult to use some kinds of medical agents for the prefilled syringe.

In a prefilled syringe to be stored for a long time with the medical agent solution being filled therein, it can be desirable to keep the medical agent solution stable for a long time and reduce or eliminate reliance on the use of the lubricant.

As disclosed in Japanese Patent Application Laid-Open No. 62-32970, Japanese Patent Application Laid-Open No. 2002-089717, and U.S. Pat. No. 7,111,848, prefilled syringes are disclosed in which the surface of the gasket is covered with a fluorine resin which is a material having a lower friction coefficient than the material of the gasket body to eliminate the use of the lubricant.

A gasket having the coating layer composed of a fluorine resin, a silicon resin, and a urethane resin, is disclosed in Japanese Patent Application Laid-Open No. 2004-321614. A gasket having the coating layer composed of a film made of the composition containing a sliding property-imparting component and a flexibility-imparting component and of fine solid particles held by the film to form the rough surface on the gasket, is disclosed in Japanese Patent Application Laid-Open No. 2006-167110, Japanese Patent Application Laid-Open No. 2008-287, and U.S. Patent Application Publication No. 2007-0299402. As also disclosed in International Publication No. WO 2009/084646 and U.S. Patent Application Publication No. 2010/0324501, a composition is disclosed containing a sliding property-imparting component, a flexibility-imparting component, and an adhesive component, and a gasket having the coating layer not containing the fine solid particles is disclosed.

The documents discussed herein include:

Patent document 1: Japanese Patent Application Laid-Open No. 62-32970;

Patent document 2: Japanese Patent Application Laid-Open No. 2002-089717;

Patent document 3: U.S. Pat. No. 7,111,848;

Patent document 4: Japanese Patent Application Laid-Open No. 2004-321614;

Patent document 5: Japanese Patent Application Laid-Open No. 2006-167110;

Patent document 6: Japanese Patent Application Laid-Open No. 2008-287 (U.S. Patent Application Publication No. 2007/029940); and Patent document 7: WO Publication No. 2009/084646 (U.S. Patent Application Publication No. 2010/0324501).

SUMMARY

The gaskets disclosed in Japanese Patent Application Laid-Open No. 62-32970), Japanese Patent Application Laid-Open No. 2002-089717, and U.S. Pat. No. 7,111,848 can be effective depending on conditions of use. But in the preparation of a prefilled syringe for discharging the medical agent solution therefrom under a high pressure and having the performance of stably discharging the medical agent solution therefrom little by little with a very high accuracy for a long time by using a syringe pump or the like, liquid-tightness and sliding performance which can be fundamental performance characteristics of the syringe can be in a trade-off relationship. A syringe which allows these performance characteristics to be compatible with each other at a high level and having a higher performance is desirable.

In administration of the medical agent solution by using the syringe pump, when the medical agent solution is discharged therefrom in a condition where the flow rate is relatively low (for example, in a syringe with a diameter of approximately 24 mm, a locomotive speed of the gasket is approximately 2 mm/h when a discharge speed is 1 mL/h), wherein the flow of the medical agent solution is not visible, an unstable discharge state called pulsation can occur. There is a concern that this can adversely affect accurate administration of the medical agent solution.

The gaskets disclosed in Japanese Patent Application Laid-Open No. 2004-321614 which are suggested to balance liquid-tight property with slidability, Japanese Patent Publication Laid-Open No. 2006-167110, and Japanese Patent Application Laid-Open No. 2008-287, U.S. Patent Application Publication No. 2007/029940, are liquid-tight and have stable sliding performance without applying a lubricant to the sliding surface thereof. But the former can have a problem in terms of production and cost in that materials forming the coating layer can be used in a wide variety. The latter can have a problem that the solid fine particles held by the coating layer can separate therefrom and insoluble fine particles can be generated in the medical agent solution. The gasket disclosed in International Publication No. WO 2009/084646, U.S. Patent Application Publication No. 2010/0324501 attempt to address these problems. But as a production principle thereof, the reactive silicone having the silanol group at the terminal thereof is hardened in the condensation reaction by using an organic tin compound used as the catalyst to form the coating layer. The organic tin compound used as the catalyst is employed in the gasket of International Publication No. WO 2009/084646, U.S. Patent Application Publication No. 2010/0324501. In light of the poisonous property of the organic tin compound and the influence thereof on the environment, investigations are being conducted for regulating the use of the organic tin compound depending on the specific area and use.

According to an exemplary aspect, disclosed is a medical appliance having a slidable coating layer in which a coating layer can be formed of a composition which reduces or eliminates the need for the use of an organic tin compound as a hardening catalyst and which has a stable sliding performance without applying a lubricant to a sliding surface thereof. According to an exemplary aspect, disclosed is a syringe including a gasket having stable sliding performance.

An exemplary medical appliance having a slidable coating layer is described below. The medical appliance having a slidable (slideable) coating layer can move in contact with an inner surface of a medical member or that of a lumen and can have a slidable coating layer formed at a part thereof which contacts the medical member or the lumen. The slidable coating layer can be formed of a composition which does not contain solid fine particles and contains a silicone-based resin which is a product of an addition reaction between silicone having a vinyl group and silicone having a hydrogen group bonded to a silicon atom.

An exemplary syringe is described below. The syringe can have an outer cylinder for the syringe; a gasket, for the syringe, which can be the above-described medical appliance having a slidable coating layer slidably accommodated inside the outer cylinder; and a plunger which can be mounted on the gasket.

A medical appliance having a slidable coating layer which moves in contact with the inner surface of the medical member or that of the lumen, can have the slidable coating layer formed at a part thereof which contacts the medical member or the lumen. The slidable coating layer can be formed of a composition which does not contain solid fine particles and contains the silicone-based resin which is a product of an addition reaction between the silicone having the vinyl group and the silicone having the hydrogen group bonded to the silicon atom.

For example, in the slidable coating layer of the medical appliance having a slidable coating layer, a product of an addition reaction between the silicone having the vinyl group and the silicone having the hydrogen group bonded to the silicon atom can be used as the silicone-based resin. In an exemplary embodiment, at the hardening reaction time in forming the coating layer, an organic tin compound is not used as a catalyst. In the case where the use of the organic tin compound is restricted or prohibited in the future, an exemplary medical appliance having a slidable coating layer can be stably supplied to the market.

Further, unlike a coating layer containing the fine particles, an exemplary slidable coating layer of the medical appliance having a slidable coating layer can have a favorable sliding property when it slides at a low speed. In addition, in an exemplary embodiment, while the medical appliance having a slidable coating layer is in storage, the medical member (for example, outer cylinder for syringe) and the medical appliance having a slidable coating layer (for example, gasket) do not stick to each other. Therefore in using the syringe, a smooth initial motion can be accomplished when the syringe is used.

According to an exemplary aspect, a coated medical appliance is disclosed, comprising: a medical appliance which is configured to move while being in contact with an inner surface of a medical member or an inner surface of a lumen; and a slidable coating layer, wherein the slidable coating layer is formed at a part of the medical appliance for contacting said medical member or said lumen, wherein said slidable coating layer is formed of a composition which does not contain solid fine particles, wherein said slidable coating layer contains a silicone-based resin which is a product of an addition reaction between silicone having a vinyl group and silicone having a hydrogen group bonded to a silicon atom.

According to an exemplary aspect, a syringe is disclosed, comprising: an outer cylinder; and an exemplary coated medical appliance, wherein the coated medical appliance is a gasket slidably accommodated inside said outer cylinder; and a plunger which is mounted or capable of being mounted on said gasket.

BRIEF DESCRIPTION OF THE DRAWINGS

FIG. 6 is a sectional view of a guide wire of an embodiment of a medical appliance having a slidable coating layer, in accordance with an exemplary aspect.

DETAILED DESCRIPTION

An exemplary medical appliance having a slidable coating layer is described below.

A medical appliance 1 having a slidable coating layer moves in contact with an inner surface of a medical member or that of a lumen and has the slidable coating layer 3 formed at a part thereof which contacts the medical member or the lumen. The slidable coating layer 3 is formed of a composition which does not contain solid fine particles and contains a silicone-based resin which is a product formed by addition reaction between silicone having a vinyl group and silicone having a hydrogen group bonded to a silicon atom.

In an exemplary embodiment, the composition forming the coating layer 3 does not contain a tin-based compound. In an exemplary embodiment, the composition forming the coating layer 3 contains a platinum group metal-based catalyst. As described later, the silicone-based resin of the composition forming the coating layer 3 can be formed by hydrosilylation between the vinyl group of the silicone and silicon bonded to the hydrogen group, of the silicone, bonded to the silicon atom.

An exemplary medical appliance having a slidable coating layer is described below in which the medical appliance having a slidable coating layer is applied to a gasket for a syringe and to the syringe. A gasket of an exemplary embodiment is described below.

Figure 1:
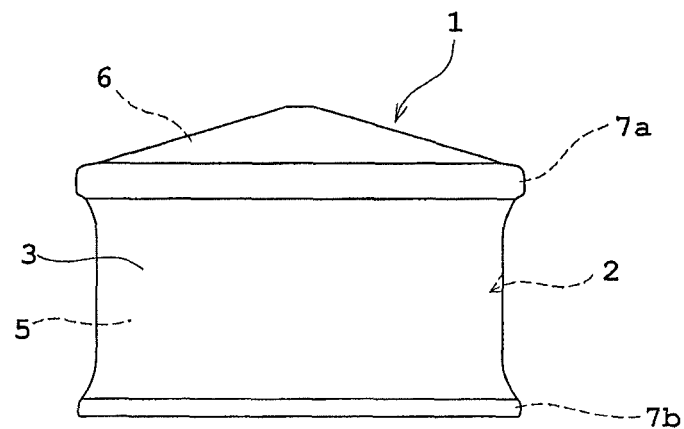
FIG. 1 is a front view of a gasket of an embodiment of a medical appliance having a slidable coating layer, in accordance with an exemplary aspect.
Figure 2:
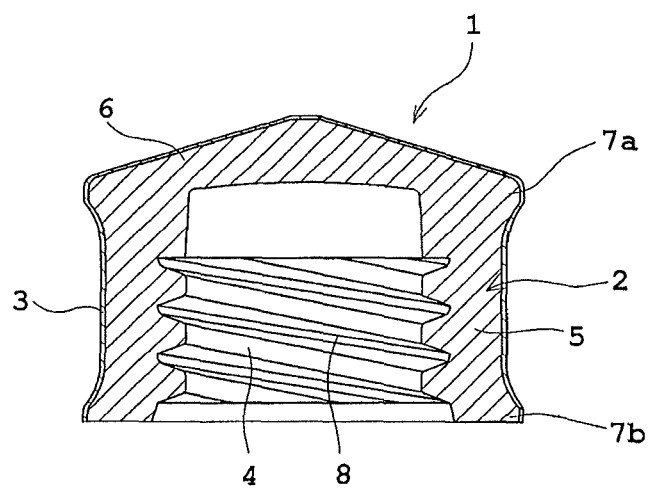
FIG. 2 is a sectional view of the gasket shown in FIG. 1, in accordance with an exemplary aspect.
Figure 3:
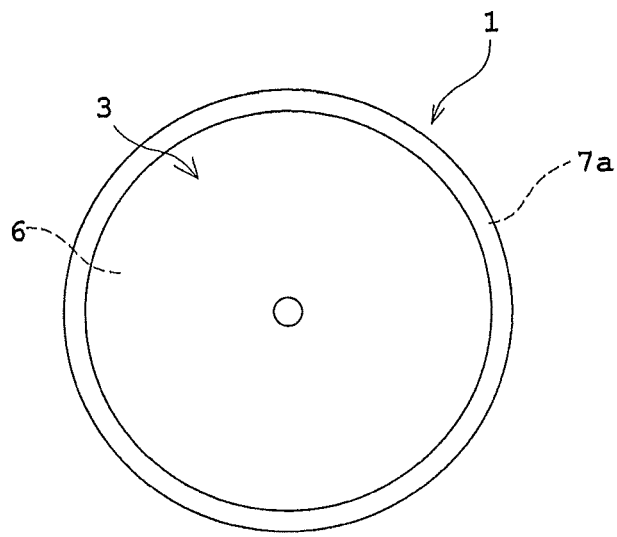
FIG. 3 is a plan view of the gasket shown in FIG. 1, in accordance with an exemplary aspect.
Figure 4:
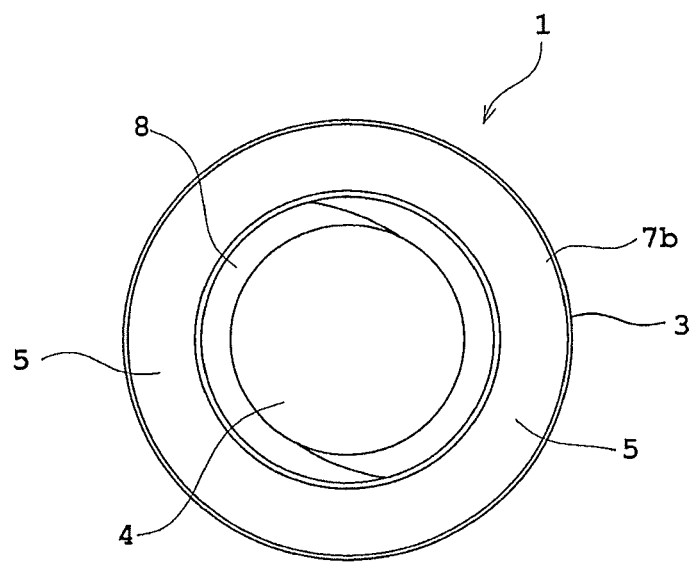
FIG. 4 is a bottom view of the gasket shown in FIG. 1, in accordance with an exemplary aspect.
Figure 5:
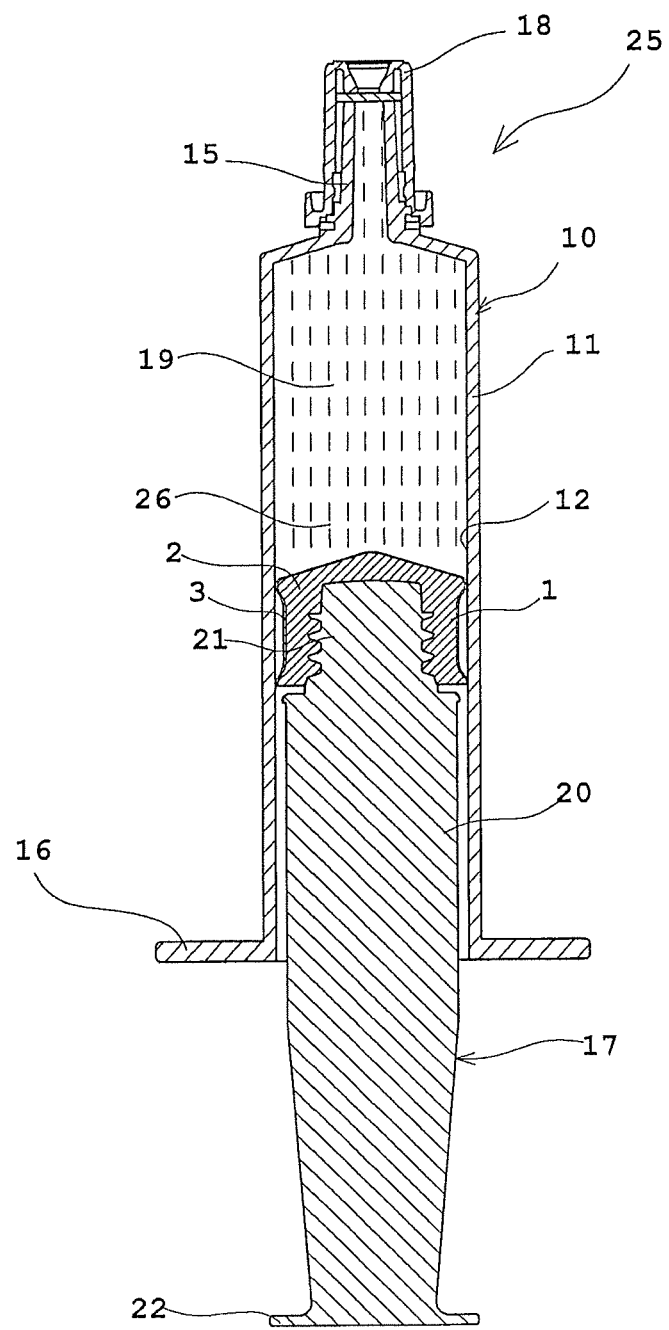
FIG. 5 is a sectional view of a prefilled syringe in which the gasket shown in FIG. 1 is used, in accordance with an exemplary aspect.

FIG. 1 is a front view showing a gasket of an exemplary embodiment. FIG. 2 is a sectional view of the gasket shown in FIG. 1. FIG. 3 is a plan view of the gasket shown in FIG. 1. FIG. 4 is a bottom view of the gasket shown in FIG. 1. FIG. 5 is a sectional view of a prefilled syringe in which the gasket shown in FIG. 1 is used.

In an exemplary embodiment, the medical appliance having a slidable coating layer of an exemplary embodiment is a gasket 1 for a syringe and liquid-tightly and slidably accommodated inside an outer cylinder 11, for the syringe, which is a medical member.

The gasket 1 which is the medical appliance having a slidable coating layer slidably contacts the inside of the outer cylinder of the syringe and has the coating layer 3 formed at a part thereof which contacts the syringe. The coating layer 3 is formed of the composition which does not contain the solid fine particles and contains the silicone-based resin which is a product of an addition reaction between the silicone having the vinyl group and the silicone having the hydrogen group bonded to the silicon atom.

Because the coating layer is formed of the above-described composition in the gasket of an exemplary embodiment, the coating layer can have a more favorable sliding performance than a coating layer containing fine particles when the gasket slides at a low speed. In addition, the gasket does not stick to the syringe during the storage of the syringe in an exemplary embodiment. Therefore, when the syringe is used, a smooth initial motion of the gasket can be accomplished, a rapid injection of a medical agent can be reduced or avoided, and the medical agent can be injected at a constant speed.

Even in a sucking operation to be often performed to check whether a blood vessel has been secured, for example, the possibility of the separation of the fine particles cannot be denied in the case of a gasket having the coating layer containing the fine particles. On the other hand, because the fine particles are not contained in the coating layer of an exemplary embodiment, the gasket can provide a benefit in that there is no risk of floating of the fine particles in the medical agent solution.

The gasket 1 of an exemplary embodiment is used for the syringe and liquid-tightly and slidably accommodated inside the outer cylinder 11 for the syringe. The gasket 1 has the coating layer 3 disposed at the part thereof where the coating layer 3 contacts the outer cylinder 11. The coating layer 3 contains a silicone resin to be described later. The gasket 1 has a body part (in other words, a core part) 2 and the coating layer 3 formed on at least the part, of an outer surface of the core part 2, where the coating layer 3 contacts an inner surface 12 of the outer cylinder 11. The coating layer 3 may be formed on the entire outer surface of the core part 2.

As shown in FIGS. 1, 2, and 5, the core part 2 of the gasket 1 for the syringe has a body portion 5 extending in an almost equal diameter, a tapered portion 6 disposed at a distal side of the body portion 5 and decreasing taperingly to the distal end thereof in its diameter, a plunger-mounting portion 4 disposed inside the body portion 5 from a proximal end thereof toward the distal end thereof; a distal-side annular rib 7a disposed on a side surface of a distal portion of the body portion 5, and a proximal-side annular rib 7b disposed on a side surface of a proximal portion of the body portion 5. As shown in FIGS. 2 and 4, the plunger-mounting portion 4 is formed as an approximately columnar concave portion which is disposed inside the body portion 5 and extends from the proximal end of the body portion 5 to a position in the vicinity of the distal end thereof. A screwing portion 8 capable of screwing on a screwing portion formed at a distal end of a plunger 17 is formed on a side surface of the above-described concave portion. A distal-end surface of the concave portion is formed almost flatly. The plunger-mounting portion 4 does not necessarily have to be formed as the screwing portion, but may be formed as an engaging portion which engages the distal portion of the plunger or may be formed in combination of the screwing portion and the engaging portion. An operation of mounting the plunger on the plunger-mounting portion is performed by screwing the plunger on the plunger-mounting portion. But a state in which the engaging portion engages the distal portion of the plunger may be held by an engaging portion formed separately from the screwing portion.

The outer diameters of the annular ribs 7a and 7b are formed a little larger than the inner diameter of the outer cylinder 11 for use in the syringe. Therefore the annular ribs 7a and 7b compressively deform inside the outer cylinder 11. In an exemplary embodiment, two annular ribs are formed, but one or three or more annular ribs may be formed.

As materials composing the core part (body portion of gasket) 2, an elastic material can be employed. The elastic material to be used for the core part 2 is not limited to a specific one. Rubber materials (vulcanized rubber materials) such as natural rubber, isoprene rubber, butyl rubber, chloroprene rubber, nitrile-butadiene rubber, styrene-butadiene rubber, and silicone rubber; styrene-based elastomers and hydrogenated styrene-based elastomers; and mixtures of the styrene-based elastomers and polyolefins such as polyethylene, polypropylene, polybutene, and α-olefin copolymers; mixtures of the styrene-based elastomers and oil such as liquid paraffin, process oil; and mixtures of the styrene-based elastomers and powdery inorganic substances such as talc, cast, mica, and the like can be employed. It is possible to use polyvinyl chloride-based elastomers, olefin-based elastomers, polyester-based elastomers, polyamide-based elastomers, polyurethane-based elastomers, and mixtures of these elastomers as materials composing the core part 2. As the composing material, the butyl rubber is exemplary from the standpoint that it has elastic properties and can be sterilized by a high-pressure steam. The diene-based rubber and the styrene-based elastomers are exemplary from the standpoint that these substances can be sterilized by γ rays and electron beams.

In an exemplary embodiment, the coating layer 3 is formed at least at the portions where the annular ribs are disposed. In an exemplary embodiment, the coating layer 3 is formed at the distal-side annular rib 7a and the proximal-side annular rib 7b. The coating layer 3 may be formed on the entire outer surface of the core part 2. The thickness of the coating layer 3 can be 1 to 30 μm, for example, 3 to 10 μm. When the thickness of the coating layer 3 is not less than 1 μm, the coating layer 3 can display a desirable slidable performance. When the thickness of the coating layer 3 is not more than 30 μm, the coating layer 3 does not, for example, adversely affect the elasticity of the gasket. In an exemplary embodiment, the coating layer 3 does not contain solid fine particles.

The coating layer 3 is composed of a resin containing a material having a lower friction coefficient than the elastic material composing the core part 2. The resin of the coating layer 3 is silicone-based. It is possible to use both a solvent-based coating solution dissolved in an organic solvent and a water-based coating solution emulsified and dispersed in water. But in the case of the solvent-based coating solution, there can be a concern about the influence thereof on the material of the gasket and about the presence of a residual solvent. Therefore the water-based coating solution is exemplary because the water-based coating solution can allow the gasket to have a higher aptitude than the solvent-based coating solution as a medical agent solution accommodation container.

The coating layer 3 includes the silicone to be obtained by hardening the product formed as a result of an addition reaction made between the silicone having the vinyl group and the silicone having the hydrogen group bonded to the silicon atom by using the catalyst containing platinum. In an exemplary embodiment, the coating layer 3 does not contain the solid fine particles. The silicone can be thermosetting silicone or room-temperature curing silicone. From the standpoint of workability, the thermosetting silicone can be exemplary. In an exemplary embodiment, the coating layer 3 formed on the gasket does not contain the "solid fine particle". The "solid fine particle" herein means a particle having a size to such an extent as to affect the roughness of the outer surface of the coating layer 3 when the coating layer 3 is formed. Specifically, the "solid fine particle" means a particle having a diameter not less than 10% of the thickness of the coating layer 3.

Because the gasket 1 has the above-described coating layer 3, the gasket 1 has a stable sliding performance without applying a lubricant to the sliding surface thereof and is capable of maintaining sealing performance inside the medical agent accommodation space. It is exemplary that the initial sliding resistance value of the coating layer (in other words, gasket having coating layer) is not more than a maximum value of the dynamic sliding resistance value thereof. The gasket satisfying the above-described characteristic is capable of starting desirable initial sliding and does not make an excessive initial movement.

An exemplary method of forming the coating layer 3 is described below. In an exemplary method of forming the coating layer, the coating layer is obtained by applying a coating solution to the clean surface of the gasket and thereafter hardening it. At this time, as the method of applying the coating solution to the surface of the gasket, it is possible to use any suitable method such as a dipping method, a spraying method, and the like. It is exemplary to apply (spray) the coating solution to the surface of an object to be coated with the object being rotated (for example, at 100 to 600 rpm). In spraying the coating solution to the surface of the gasket, it can be desirable to do so after heating a portion of the gasket to be coated to 60 to 120 degrees C. Thereby the coating solution can be rapidly fixed to the surface of the portion of the gasket to be coated without water repellence.

As the method of hardening the coating solution, it may be left at a normal temperature, but it is exemplary to harden it by heating it. The method of thermally hardening the coating solution is not limited to a specific method, provided that the base material of the gasket is not modified or deformed. Hot-air drying, and a drying oven using infrared rays, and the like are exemplified. Alternatively the method of hardening the coating solution can be carried out by any suitable method such as a method of using a decompression drier. The thickness of the coating layer can be 1 to 30 μm, for example, 3 to 10 μm. Such a coating layer can be easily formed by appropriately controlling the concentration of a mixed solution, the dipping method, and the spraying method.

As the coating solution, a water-based coating solution in which reactive silicone is emulsified and dispersed in water is exemplary because as described above, the water-based coating solution can allow the gasket to have an aptitude easily as the medical agent solution accommodation container. An exemplary coating solution contains not only the reactive silicone which becomes a specific silicone-based resin after undergoing a reaction, but also a specific auxiliary agent for obtaining adhesion between the coating layer 3 and the core part 2 and enhancing the strength of the coating layer to limit or prevent the coating layer 3 from peeling off the core part 2 or the coating layer 3 from being destroyed of itself when the gasket slides. An exemplary composition of the water-based coating solution is described below. The coating solution can at least contain the following three components. They are a component 1 which is the reactive silicone, a component 2 which is a reaction catalyst for the component 1, and a component 3 which is the auxiliary agent for limiting or preventing the coating layer 3 from peeling from the core part 2 and from being destroyed of itself. The coating solution is capable of containing additives as desired. An exemplary composition contains the component 1: the reactive silicone, the component 2: the reaction catalyst and a reaction inhibitor for the component 1, and the component 3: the auxiliary agent.

Each exemplary component is described in detail below.

The component 1 can be the combination of two kinds of components (component 1a, component 1b). The component 1a can be an emulsion of polysiloxane containing the main component of the silicone of the coating layer 3. The polysiloxane can have at least two vinyl groups in one molecule thereof. As the method of preparing the emulsion, two methods are exemplified. In one of the two methods, an emulsion of polydimethylsiloxane having at least two vinyl groups in one molecule thereof can be prepared by emulsifying and polymerizing cyclic siloxane (hereinafter referred to as "emulsion polymerization method"). In the other method, an emulsion of the polysiloxane can be prepared by dispersing the polysiloxane having at least two vinyl groups in one molecule thereof in water and emulsifying it (hereinafter referred to as "dispersion emulsification").

In the emulsion polymerization method, the emulsion of the polysiloxane having at least two vinyl groups in one molecule can be prepared by dispersing the cyclic siloxane, the siloxane or silane having the vinyl group and an acid emulsifier in water and emulsifying and polymerizing the cyclic siloxane, the siloxane or the silane. As the cyclic siloxane, hexamethylcyclotrisiloxane, octamethylcyclotetrasiloxane, decamethylcyclopentasiloxane, dodecamethylcyclohexasiloxane, hexaethylcyclotrisiloxane, hexaphenylcyclotrisiloxane, octaphenylcyclotetrasiloxane, triphenyltrimethylcyclotrisiloxane, and (3,3,3-trifluoropropyl)methylcyclotrisiloxane can be employed. As the siloxane or the silane having the vinyl group, 1,3,5-trivinyl-1,3,5-trimethylcyclotrisiloxane, 1,3,5,7-tetravinyl-1,3,5,7-tetramethylcyclotetrasiloxane, pentavinylpentamethylcyclopentasiloxane, vinyltrimethoxysilane, vinyltriethoxysilane, and tetrakis(vinyldimethylsiloxy)silane can be employed. The mixing ratio (mole/mole) of the siloxane or the silane having the vinyl group to the cyclic siloxane can be 0.01 to 0.3, for example, 0.05 to 0.2. As the acid emulsifier, any suitable acid-type anion surface active agent can be used. As the anion surface active agent, organic sulfonates, higher alcohol sulfates, and higher alcohol ethoxylate sulfates can be employed. Straight-chain alkyl benzene sulfonic acid can be employed. As an emulsification apparatus to be used in the dispersion and the emulsification, it is possible to use a high-speed rotation type emulsification apparatus such as a homomixer type, a comb teeth type, and an intermittent jet stream generation type for rough emulsification. It is possible to use a pressure-type homogenizer for fine emulsification. It is exemplary to so select the emulsification apparatus and a treatment condition as to obtain an emulsion of fine particles having an average diameter of about 1 μm in the rough emulsification and an emulsion of finer particles having an average diameter not exceeding 500 nm in the fine emulsification. When the average particle diameter is more than hundreds of nanometers after the fine emulsification finishes, a creaming phenomenon can occur owing to coalescence of the fine particles, which can be undesirable in terms of the stability of the emulsion. The emulsion polymerization can be performed by heating a finely emulsified product. It is exemplary to heat the finely emulsified product at 60 to 80 degrees C. and for five to eight hours. The fine particles in the emulsion obtained by the emulsion polymerization are the polysiloxane having at least two vinyl groups in one molecule thereof. The molecular weight of the polysiloxane can be 60,000 to 400,000. The content of the vinyl group can be 0.5 to 10 wt %. The emulsion concentration of the component 1a can be 30 to 60%.

In the dispersion emulsification method, the emulsion of the polysiloxane can be prepared by dispersing the polysiloxane having at least two vinyl groups in one molecule thereof and the emulsifier in water and emulsifying the polysiloxane. As the polysiloxane having at least two vinyl groups in one molecule thereof, polydimethylsiloxane having the vinyl group at both terminals thereof, poly(diphenylsiloxane-dimethylsiloxane) having the vinyl group at both terminals thereof, polyphenylmethylsiloxane having the vinyl group at both terminals thereof, poly(vinylphenylsiloxane-phenylmethylsiloxane) having the vinylphenylmethyl group at both terminals thereof, poly(trifluoropropyl methyl siloxane-dimethylsiloxane) having the vinyl group at both terminals thereof, poly(diethylsiloxane-dimethylsiloxane) having a vinyl group at both terminals thereof, polyvinylmethylsiloxane having a trimethylsilyl group at both terminals thereof, poly(vinylmethyl siloxane-dimethylsiloxane) having the trimethylsilyl group at both terminals thereof, polyvinylmethoxysiloxane, polyvinylethoxysiloxane, and poly(vinylethoxysiloxane-propylethoxysiloxane) can be employed. The viscosity of the polysiloxane can be 100 to 10,000 mPa, for example, 500 to 5,000 mPa. When the viscosity of the polysiloxane exceeds 10,000 mPa, in the dispersion and emulsification to be performed by a normal emulsification apparatus, it can be difficult to accomplish an intended fine atomization. The molecular weight of the polysiloxane can be 5,000 to 60,000 for example, 10,000 to 50,000. The content of the vinyl group of the polysiloxane can be 0.05 to 2 wt %. As the emulsifier, it is possible to use any suitable anion surface active agents and nonionic surface active agents. As the anion surface active agent, it is possible to use aliphatic monocarboxylates, polyoxyethylene alkyl ether carboxylates, N-acyl sarcosinates, N-acylglutamates, dialkyl sulfosuccinates, alkane sulfonates, alpha-olefin sulfonates, straight-chain alkylbenzene sulfonates, molecular-chain alkylbenzene sulfonates, naphthalene sulfonate-formaldehyde condensates, alkylnaphthalene sulfonates, N-methyl-N-acytaurin, alkyl sulfates, polyoxyethylene alkyl ether sulfates, fatty acid sulfates, alkyl phosphates, polyoxyethylene alkyl ether sulfates, and polyoxyethylene alkyl phenyl ether sulfates. As the nonionic surface active agent, it is possible to use polyoxyethylene alkyl ether, polyoxyalkylene derivatives, polyoxyethylene alkyl phenyl ether, polyoxyethylene sorbitan fatty acid ester, fatty acid alkanolamide, glycerin fatty acid ester, sorbitan fatty acid ester, polyoxyethylenealkylamine, and alkyl alkanolamide. Of these surface active agents, the straight-chain alkylbenzene sulfonates are exemplary. As the emulsification apparatus to be used in the dispersion and emulsification, it is possible to use the high-speed rotation type emulsification apparatus such as the homo-mixer type, the comb teeth type, and the intermittent jet stream generation type for the rough emulsification and use the pressure-type homogenizer for the fine emulsification. It is exemplary to so select the emulsification apparatus and the treatment condition as to obtain the emulsion of fine particles having the average diameter of about 1 μm in the rough emulsification and the emulsion of finer particles having the average diameter of not exceeding 500 nm in the fine emulsification. When the average particle diameter is more than hundreds of nanometers after the fine emulsification finishes, the creaming phenomenon can occur owing to the coalescence of the fine particles, which can be undesirable in terms of the stability of the emulsion.

The component 1b can be the emulsion of the polysiloxane contained in the auxiliary component of the silicone of the coating layer 3 and can react with the polysiloxane in the component 1a which can be the main component of the silicone of the coating layer 3, thus playing the role of a crosslinking agent in the silicone of the coating layer 3. The polysiloxane can have at least two hydrogen groups bonded to silicon atom in one molecule thereof. The emulsion of the polysiloxane can be prepared by dispersing the polysiloxane and the emulsifier in water and emulsifying the polysiloxane. The method of preparing the emulsion of the polysiloxane can be carried out similarly to the dispersion emulsification method of the component 1a. As the polysiloxane having the two hydrogen groups bonded to silicon atoms in one molecule thereof, polymethylhydrosiloxane having the trimethylsilyl group at its both terminals, poly(methylhydrosiloxane-dimethylsiloxane) having the trimethylsilyl group at its both terminals, polymethylhydrosiloxane having the trimethylsilyl group at its both terminals, and poly(methylhydrosiloxane-octylmethylsiloxane) having the trimethylsilyl group at its both terminals can be employed. Depending on the circumstances, it can be possible to add polydimethylsiloxane having the hydrogen group bonded to the silicon atom at its both terminals, polyphenyl(dimethylhydro)siloxane having the hydrogen group bonded to the silicon atom at its both terminals, and poly(methylhydrosiloxane-phenylmethylsiloxane) having the hydrogen group bonded to the silicon atom at its both terminals to the polysiloxane so that these additives serve as a chain extender. The viscosity of the polysiloxane of the component 1b can be 2 to 1,000 mPa, for example, 10 to 500 mPa. The molecular weight of the polysiloxane can be 500 to 50,000, for example, 1,000 to 20,000. The content of the hydrogen group bonded to the silicon atom can be 100 mol % in the case of the polymethylhydrosiloxane having the trimethylsilyl group at its both terminals, 3 to 50 mol % in the case of the poly(methylhydrosiloxane-dimethylsiloxane) having the trimethylsilyl group at its both terminals and the poly(methylhydrosiloxane-octylmethylsiloxane) having the trimethylsilyl group at its both terminals, and 0.01 to 0.5 wt % in the case of the polysiloxane having the hydrogen group at its both terminals. The emulsion concentration of the component 1b can be 30 to 60%. As the mixing amount of the component 1b to be contained in the coating solution, the ratio (mole ratio) of the amount of the hydrogen group of the component 1b to the amount of the vinyl group of the component 1a can be 0.5 to 2.0, for example, 0.8 to 1.5.

The component 2 can serve as the catalyst in the reaction between the component 1a and the component 1b as one of its roles. As the reaction catalyst, the component 2 can contain at least one platinum-group metal for accelerating the hydrosilylation between the vinyl group of the component 1a and the hydrogen group of the component 1b. As the platinum-group metal catalyst (platinum group catalyst), catalysts of platinum group, palladium group, and rhodium group can be employed. Of the above-described catalysts, the platinum group catalyst is exemplary. For example, chloroplatinic acid, alcohol-modified chloroplatinic acid, complexes of chloroplatinic acid and ketones, complexes of the platinum and olefin, and complexes of the platinum and vinylsiloxane can be employed. For example, the main component of the component 1a and that of the component 1b can be the polysiloxane. Thus in consideration of the compatibility between the polysiloxane and the catalyst of the above-described catalysts, the complex of the platinum and the vinylsiloxane is exemplary. For example, a solution of a vinyl methyl cyclic siloxane which is a platinum-vinylsiloxane carbonyl cyclo-vinylmethylsiloxane complex, a solution of the polydimethylsiloxane which has the vinyl group at both terminals thereof and is a platinum-divinyltetramethyldisiloxane complex, and a solution of cyclic methylvinylsiloxane which is a platinum-cyclovinylmethylsiloxane complex can be employed. The concentration of the platinum in these solutions can be 1 to 3 wt %. The mixing amount of the component 2 to be contained in the coating solution can be 1 to 1,000 ppm, for example, 5 to 500 ppm, for example, 50 to 200 ppm for the polysiloxane of the component 1a in terms of the amount of the platinum. An exemplary form of the component 2 is the emulsion to be obtained by dispersing the platinum-vinylsiloxane complex and the emulsifier in water and emulsifying the platinum-vinylsiloxane complex. The method of preparing the emulsion can be the same as that of forming the emulsion of the component 1 to be obtained by carrying out the dispersion emulsification method. As another role of the component 2, the component 2 can serve as a reaction inhibitor in the reaction between the component 1a and the component 1b. For example, the component 2 can serve as an addition reaction inhibitor for obtaining stability by appropriately inhibiting the hydroxylation between the vinyl group of the component 1a and the hydrogen group of the component 1b while the coating solution is in storage and while an operation is being performed. As the addition reaction inhibitor, 3-methyl-1-butyne-3-ol, 3-methyl-1-pentyne-3-ol, 3,5-dimethyl-1-hexyne-3-ol, 1-ethynylcyclohexanol, 3-methyl-3-trimethylsiloxane-1-butyne, 3-methyl-3-trimethylsiloxane-1-pentyne, 3-methyl-3-trimethylsiloxne-1-hexyne, 1-ethynyl-1-trimethylsiloxycyclohexane, bis(2,2-dimethyl-3-butynoxy)dimethylsilane, 1,3,5,7-tetraethyl-1,3,5,7-tetravinylcyclotetrasiloxane, and 1,1,3,3-tetramethyl-1,3-divinyldisiloxane can be employed. The mixing amount of the addition reaction inhibitor to be contained in the coating solution can be 1 to 10 wt %, for example, 0.1 to 2 wt % for the polysiloxane of the component 1a.

The component 3 contains an auxiliary agent for limiting or preventing the coating layer 3 from peeling off the core part 2 and from being destroyed. As the auxiliary agents of the component 3, alkyl alkoxysilane, phenylalkoxysilane, alkylphenoxysilane, aminoalkylalkoxysilane, and glycidoxyalkylalkoxysilane are exemplary. The alkyl alkoxysilane has at least one alkyl group having a carbon number of 1 to 20 and at least one alkoxy group having a carbon number of 1 to 4. Exemplary auxiliary agent of the component 3 includes methyltrimethoxysilane, methyltriethoxysilane, methyltriisobutoxysilane, methyltributoxysilane, methyl sec-trioctyloxysilane, isobutyltrimethoxysilane, cyclohexylmethyldimethoxysilane, diisopropyldimethoxysilane, propyltrimethoxysilane, diisobutyldimethoxysilane, n-octylmethoxysiloxane, ethyltrimethoxysilane, dimethyldimethoxysilane, octyltriethoxysilane, hexyltrimethoxysilane, hexyltriethoxysilane, octamethylcyclotetrasiloxane, methyltri(acryloyloxyethoxy)silane, octyltriethoxysilane, lauryltriethoxysilane, stearyltrimethoxtsilane, stearyltrimethoxtsilane, ethyltriethoxysilane, propyltriethoxysilane, butyltriethoxysilane, butyltrimethoxysilane, pentyltrimethoxysilane, pentyltriethoxysilane, heptyltrimethoxysilane, heptyltriethoxysilane, octyltrimethoxysilane, nonyltrimethoxysilane, nonyltriethoxysilane, decyltrimethoxysilane, decyltriethoxysilane, undecyltrimethoxysilane, undecyltriethoxysilane, dodecyltrimethoxysilane, dodecyltriethoxysilane, tridodecyltrimethoxysilane, tridodecyltriethoxysilane, tetradecyltrimethoxysilane, tetradecyltriethoxysilane, pentadecyltrimethoxysilane, pentadecyltriethoxysilane, hexadecyltrimethoxysilane, hexadecyltriethoxysilane, heptadecyltrimethoxysilane, heptadecyltriethoxysilane, octadecyltrimethoxysilane, octadecyltriethoxysilane, nonadecyltrimethoxysilane, nonadecyltriethoxysilane, eicosyltrimethoxysilane, and eicosyltriethoxysilane are exemplary. As the alkylphenoxysilane, for example, methyltriphenoxysilane is exemplary. As the phenoxyalkoxysilane, phenyltrimethoxysilane, phenyltriethoxysilane, diphenyldimethoxysilane, and diphenyldiethoxysilane are exemplary. The mixing amount of the above-described auxiliary agents to be contained in the coating solution can be 0.01 to 10 wt %, for example, 0.1 to 5 wt % for the polysiloxane of the component 1a. When the mixing amount of these auxiliary agents is less than 0.1 wt %, it can be difficult to obtain sufficient stability of the coating solution. When the mixing amount thereof is more than 10 wt %, the adhesion between the coating layer 3 and the core part 2 can be insufficient, which can be undesirable.

As other exemplary auxiliary agents of the component 3, alkoxysilane having an ureido group (—NH—CO—NH$_2$) and alkoxysilane having an uraren group (—NH—CO—NH—) are exemplified. As the alkoxysilane having the ureido group (—NH—CO—NH$_2$) and the alkoxysilane having the uraren group (—NH—CO—NH—), γ-ureidopropyltriethoxysilane, γ-ureidopropyldiethoxymethylsilane, methylurarenpropyldimethoxymethylsilane, 3-[(2-ureidoethyl)ureil]propyltrimethoxysilane, O═C[NHCH$_2$CH$_2$CH$_2$Si(OC$_2$H$_5$)$_3$]$_2$ can be employed. The γ-ureidopropyltriethoxysilane is exemplary because it is water-soluble and thus can be dispersed in water in mixing it with other components of the coating solution to prepare the emulsion and in addition it can be easily obtained in a commercial circulation.

As still other exemplary auxiliary agents of the component 3, the product of a reaction between the alkoxysilane having an amino group and dicarboxylic anhydride is exemplary. The reaction product can be obtained by mixing the alkoxysilane having the amino group and the dicarboxylic anhydride with each other by, for example, setting the mixing ratio (mole ratio) of the amino group to the carboxylic acid to 0.5 to 2, for example, 0.8 to 1.2 and allowing both substances to react with each other in a solvent for several hours, for example, ten or more hours, at not less than a room temperature nor more than 90 degrees C. As solvents to be used, alcohols such as methanol, ethanol, and isopropanol; and ketones such as acetone and methyl ethyl ketone can be employed. The reaction between the above-described two substances can be conducted while the solvent is refluxing. As the alkoxysilane having the amino group, 3-aminopropyltriethoxysilane, 3-(2-aminoethyl)aminopropyltrimethoxysilane, 3-(2-aminoethyl)aminopropylmethyldimethoxysilane, 3-aminopropyltrimethoxysilane, and 3-phenylaminopropyltrimethoxysilane are exemplary. As the dicarboxylic anhydride, phthalic anhydride, succinic anhydride, maleic anhydride, and glutaric anhydride can be employed. The mixing amount of the above-described auxiliary agents to be contained in the coating solution can be 1 to 10 wt %, for example, 3 to 8 wt % for the polysiloxane of the component 1a. When the mixing amount of these auxiliary agents is less than 1 wt %, the adhesion between the coating layer 3 and the core part 2 can be insufficient. When the mixing amount of these auxiliary agents is more than 10 wt %, the flexibility and expansibility of the coating layer 3 can deteriorate and the adhesion between the coating layer 3 and the core part 2 can be insufficient, which can be undesirable.

As still other exemplary auxiliary agents of the component 3, glycidoxyalkylalkoxysilane may be used. As the glycidoxyalkylalkoxysilane, 3-glycidoxypropyltrimethoxysilane, 3-glycidoxypropyltriethoxysilane, 3-glycidoxypropylmethyldiethoxysilane, 3-glycidoxypropylmethyldimethoxysilane, and 2-(3,4-epoxycyclohexyl)ethyltrimethoxysilane are exemplary. The mixing amount of the above-described auxiliary agents of the component 3 to be contained in the coating solution can be 1 to 10 wt %, for example, 3 to 8 wt % for the polysiloxane of the component 1a. When the mixing amount of these auxiliary agents to be contained therein is less than 1 wt %, the adhesion between the coating layer 3 and the core part 2 can be insufficient. When the mixing amount of these auxiliary agents to be contained therein is more than 10 wt %, the flexibility and expansibility of the coating layer 3 can deteriorate and the adhesion between the coating layer 3 and the core part 2 can be insufficient, which can be undesirable. At a step of preparing the coating solution by mixing the above-described three kinds of the effective components with one another, to allow the coating solution to be uniformly emulsified, suspended, and dispersed, additives such as a surface active agent, alcohol, and the like may be used.

As the surface active agent, an anion surface active agent is exemplary. Any anion surface active agents may be used. It is possible to use aliphatic monocarboxylates, polyoxyethylene alkylether carboxylates, N-acyl sarcosinates, N-acyl-glutamates, dialkyl sulfosuccinates, alkane sulfonates, alpha olefin sulfonates, straight chain alkylbenzene sulfonates, molecular chain alkylbenzene sulfonates, naphthalene sulfonate-formaldehyde condensate, alkylnaphthalene sulfonates, N-methyl-N-acyl taurine, alkyl sulfate, polyoxyethylene alkyl ether sulfates, fat and oil sulfates, alkyl phosphates, polyoxyethylene alkyl ether sulfates, and polyoxyethylene alkyl phenyl ether sulfates. Nonionic surface active agents may be used. Any nonionic surface active agents may be used. It is possible to use polyoxyethylene alkyl ether, polyoxyalkylene derivatives, polyoxyethylene alkylphenyl ether, polyoxyethylene sorbitan fatty acid ester, fatty acid alkanolamide, glycerin fatty acid ester, sorbitan fatty acid ester, polyoxyethyleneakylamine, and alkylalkanolamide.

The syringe 10 can have the outer cylinder 11, the gasket 1 slidably accommodated inside the outer cylinder 11, and the plunger 17 which is mounted on the gasket 1 or can be mounted on the gasket 1. For example, as shown in FIG. 5, the syringe 10 can be constructed of the outer cylinder 11, for use in the syringe, which has a needle-mounting portion 15 disposed at the distal part thereof and a pair of opposed flanges 16 disposed at the proximal end thereof; the gasket 1, for use in the syringe, which is capable of liquid-tightly and airtightly sliding on an inner surface 12 of the outer cylinder 11 for use in the syringe; the plunger 17 which is mounted on the gasket 1 or can be mounted on the gasket 1 for use in the syringe; a sealing member 18 for sealing the needle-mounting portion 15 of the outer cylinder 11 for use in the syringe; and a medical agent accommodation portion 19, for accommodating a medical agent 26, which is formed among the sealing member 18, the inner surface 12 of the outer cylinder 11, and the gasket 1 for use in the syringe. Instead of the sealing member 18, a needle may be mounted on the needle-mounting portion 15. As shown in FIG. 5, the sealing member 18 may be of a type having a piercing portion into which a double ended needle can be directly inserted or may be of a type in which the medical agent cannot be discharged until the sealing member is removed. The gasket 1 can have the above-described coating layer 3. In the syringe 10, the dynamic sliding resistance value of the gasket 1 when the gasket 1 slides at a low speed (100 mm/minute) inside the outer cylinder 11 can be not more than 20N. Such a low dynamic sliding resistance value can be obtained when the gasket 1 has the above-described coating layer 3. The dynamic sliding resistance value of the gasket 1 when the gasket 1 slides at the low speed (100 mm/minute) inside the outer cylinder 11 can be 1N to 20N.

The medical appliance can be a prefilled syringe 25 composed of the syringe 10 and the medical agent 26, as shown in FIG. 5. The outer cylinder 11 for use in the syringe can be a cylindrical member having the needle-mounting portion 15 disposed at the distal part thereof and the flange 16 disposed at the proximal end thereof. The outer cylinder 11 for use in the syringe can be made of a material transparent or semi-transparent. The outer cylinder 11 can be made of a material having low oxygen permeability or low vapor permeability. The material forming the outer cylinder 11 can have a glass transition point or a melting point not less than 110 degrees C.

As materials forming the outer cylinder 11, various general-purpose rigid plastic materials can be employed. Polyolefins such as polypropylene, polyethylene, poly (4-methylpentene-1), and cyclic polyolefin; polyesters such as polyethylene terephthalate, polyethylene naphthalate, and non-crystalline polyarylate; polystyrene; polyamide; polycarbonate, polyvinyl chloride; acrylic resin; an acrylonitrile-butadiene-styrene copolymer, and non-crystalline polyetherimide are exemplary. The polypropylene, the poly (4-methylpentene-1), the cyclic polyolefin, the polyethylene naphthalate, and the non-crystalline polyetherimide are exemplary because these resins are transparent and resistant to heat sterilization. These resins can be used as materials to form containers capable of accommodating a medical agent in addition to the outer cylinder. It is also possible to use glass as a material to form the outer cylinder.

As shown in FIG. 5, the plunger 17 can have a sectionally cross-shaped body portion 20 extended axially; a plunger-side screwing portion 21, disposed at the distal part thereof, which screws on the plunger-mounting portion 4; a disk-shaped gasket-supporting portion disposed between the plunger-side screwing portion 21 and the body portion 20; a disk portion 22, for pressing use, which is disposed at the proximal end of the body portion 20; and a disk-shaped rib formed midway on the body portion 20.

The medical agent 26 can be accommodated inside the syringe 10 of an exemplary embodiment. As the medical agent 26, it is possible to use a medical agent solution and a solid agent such as a powdery medical agent and a freeze-dried medical agent. The medical agent solution, containing the surface active agent, can have a low viscosity and a high degree of penetration. Although the medical agent solution can make it difficult to allow the gasket to have sliding property and to be liquid-tight, the medical agent solution can be accommodated inside the syringe 10 which does not require silicone oil. In the case where the coating layer 3 is formed on the gasket 1 for the syringe at the part thereof which contacts the accommodated medical agent, it is possible to reduce or prevent the adsorption of the medical agent such as the medical agent solution which contains a component having a poor water solubility and has a high adsorbing property. Thus in an exemplary embodiment, such a medical agent can be employed. In an exemplary embodiment, the medical agent solution can contain a material which would otherwise be modified by an interaction with a silicone oil lubricant.

As materials composing the plunger 17 and the sealing member 18, hard resins or semi-hard resins can be used such as polyvinyl chloride, high-density polyethylene, polypropylene, polystyrene, polyethylene terephthalate, polycarbonate, acrylic resin, and the like.

The above-described syringe is an example of the medical appliance which moves in contact with the inner surface of the medical member. This type of the medical appliance is not limited to the syringe, but may be any medical appliance, provided that they slidably contact the inside of the medical member. For example, this type of the medical appliance may be a rubber stopper-provided vial container, a transfusion bag, a blood collection tube, and a decompression blood collection tube. The medical appliance is not limited to the gasket for the syringe, but may be any of an O-ring, a stopper, a cover, and the like, provided that they slidably contact the medical member. For example, the medical appliance may be a rubber stopper of the vial container, a lid of the transfusion bag, and the like.

The medical appliance may be an appliance which moves in contact with the inner surface of the lumen. The medical appliance which moves in contact with the inner surface of the lumen can include a catheter, a guide wire, a blood vessel dilation appliance, and the like. The medical appliance may be an appliance which moves in contact with the inner surface of the medical member and that of the lumen. The medical appliance which moves in contact with the inner surface of the lumen can include the catheter, the guide wire, and the blood vessel dilation appliance which are inserted into the catheter (for example, a guiding catheter) which is a medical member such that the distal portions thereof are guided to an intended portion of the lumen.

An exemplary embodiment in which the medical appliance is applied to the guide wire is described below with reference to a drawing. FIG. 6 is a sectional view of an exemplary embodiment of the guide wire.

A guide wire 50 can have an inner core 52 and a sliding film 53 enclosing the inner core 52. The guide wire of the embodiment shown in FIG. 6 can have the inner core 52 composed of the body part 52a having a high rigidity and the distal part 52b, having a smaller diameter and a lower rigidity than the body part 52a, which is formed integrally with the body part 52a, a high radiographic visualization part 54 formed at the distal end of the inner core 52, and the sliding film 53 enclosing the entire inner core 52 on which the high radiographic visualization part 54 is formed.

The inner core 52 of the guide wire 50 has the body part 52a and the distal part 52b and can be integrally formed of an elastic metal. The diameter of the distal part 52b can be so formed as to be smaller than the distal end of the body part 52a. By so forming the distal part 52b as to have a small diameter, the distal part 52b can have a lower rigidity than the body part. The diameter of the distal part 52b may be so set as to become gradually smaller toward the distal end thereof from the distal end of the body part 52a. By making the distal part of the inner core gradually smaller in its diameter, the distal part of the inner core can gradually bend when a force is applied to the distal end of the body part 52a. Thus operability can be improved.

The inner core 52 can be made of superelastic metals and stainless steels. As the superelastic metals, superelastic metallic bodies such as a TiNi alloy containing 49-58 atom % Ni, a Cu—Zn alloy containing 38.5 to 41.5 wt % Zn, a Cu—Zn—X alloy containing 1 to 10 wt % X (X=Be, Si, Al, Ga), and a Ni—Al alloy containing 36 to 38 atom % Al can be employed. The TiNi alloy is exemplary.

The outer diameter of the body part 52a of the inner core 52 can be 0.10 to 1.00 mm, for example, 0.15 to 0.40 mm. The length of the body part 52a can be 1000 to 4000 mm, for example, 1500 to 3000 mm. The buckling strength (yield stress when a load is applied) of the body part 52a can be 30 to 100 Kg/mm$^2$ (22 degrees C.), for example, 40 to 55 Kg/mm$^2$. The restoration stress (yield stress when a load is removed) of the body part 52a can be 20 to 80 Kg/mm$^2$(22 degrees C.), for example, 30 to 35 Kg/mm$^2$.

The outer diameter of the distal part 52b of the inner core 52 can be 0.03 to 0.15 mm, for example, 0.05 to 0.10 mm. The length of the distal part 52b can be 10 to 300 mm, for example, 50 to 150 mm. The bending load of the distal part 52b can be 0.1 to 10 g, for example, 0.3 to 6.0 g. The restoration load of the distal part 52b can be 0.1 to 10 g, for example, 0.3 to 6.0 g.

The diameter of the distal part of the inner core does not necessarily have to be set to the above-described range, but may be so set as to satisfy a part of the above-described range. The restoration stress of the body part and that of the distal part does not necessarily have to have an equal value, but in an exemplary embodiment, the device can be made so as to allow the restoration stress of the body part and that of the distal part to be differentiated from each other by heat-treating them in different conditions so that the body part and the distal part have an appropriate wire diameter and thus an appropriate property respectively. That is, it can be desirable to heat-treat the body part and the distal part in different conditions to allow the restoration stress of the body part to be high and that of the distal part to be flexible. In addition, the inner core 52 does not necessarily have to be composed of a single wire, but may be composed of a plurality of parallel or twisted wires so that the inner core 52 displays the above-described function, for example, a stepwise change or a continuous change.

In the example shown in FIG. 6, the high radiographic visualization part 54 is a metallic annular member, having a high radiographic visualization performance, which is fixed to the distal end of the inner core 52. For example, the high radiographic visualization part 54 can be formed of a pipe-shaped member. As metals having high radiographic visualization performance, gold, platinum, zinc, silver, bismuth, and tungsten are exemplary. Gold is exemplary.

The high radiographic visualization part 54 can be fixed to the distal end of the inner core 52 by mechanically crimping the high radiographic visualization part 54 to the distal end thereof or by soldering the high radiographic visualization part 54 to a plated or evaporated metal. The outer diameter of the high radiographic visualization part 54 can be 0.20 to 0.90 mm, for example, 0.25 to 0.40 mm. The inner diameter thereof can be 0.04 to 0.16 mm, for example, 0.06 to 0.11 mm. The length thereof can be 1.00 to 10.00 mm, for example, 1.5 to 4.0 mm. The high radiographic visualization part 54 may be composed of a coiled thin wire formed of the above-described metal having a high radiographic visualization performance. The thin wire having a diameter of 0.02 to 0.10 mm can be used. The length of the high radiographic visualization part 54 to be wound on the distal end of the inner core can be 1.0 to 10.0 mm, for example, 1.5 to 4.0 mm from the distal end thereof.

As shown in FIG. 6, the sliding film 53 coating the entire inner core 52 including the distal part thereof can have an almost uniform outer diameter. The sliding film 53 can have an almost uniform outer diameter to reduce or prevent the difference in level between the inner core 52 and the high radiographic visualization part 54 formed at the distal end of the inner core 52 from affecting the outer configuration of the guide wire 50. A film made of the same material as that of the coating layer 3 described on the gasket of the above-described embodiment can be used as the sliding film 53.

The outer diameter of the sliding film 53 can be 0.25 to 1.04 mm, for example, 0.30 to 0.64 mm. The thickness of the inner core 52 at a part thereof disposed on the body part 52a of can be 0.25 to 1.04 mm, for example, 0.30 to 0.64 mm.

In an exemplary embodiment, the distal end (the distal end of the sliding film 53) of the guide wire 50 has a curved surface, for example, a semispherical surface as shown in FIG. 6 to limit or prevent a blood vessel wall from being damaged and improve the operability of the guide wire 50. Although the entire inner core 52 of the guide wire 50 of this embodiment can be coated with the sliding film 53, the form of the inner core 52 is not limited to this one. The sliding film 53 may be so constructed as to cover a part of the inner core 52. For example, the sliding film 53 may be so constructed as to cover only the distal part of the inner core 52 or only the body part of the inner core 52.

EXAMPLES

Examples are described below. Exemplary coating solutions were prepared in accordance with methods used in Examples 1-8 and Comparison Example 1.

Example 1

(Component 1a)

125 g of octamethylcyclotetrasiloxane, 5 g of 1,3,5,7-tetravinyltetramethylcyclotetrasiloxane, 2.5 g of dodecylbenzenesulfonic acid, and 22.5 g of water were measured and put in a 300 mL tall beaker. Thereafter by using a homo mixer, the mixture was stirred at the number of rotations of 6,000 rpm for 10 minutes. Thereafter 100 g of water was gradually added to the mixture at the number of rotations of 2,000 rpm to perform rough emulsification. After defoaming was performed under a decreased pressure, the mixture was fed to a pressure-type homogenizer twice under the condition of a pressure of 300 kg/cm$^2$ to perform fine emulsification. After a finely emulsified product was allowed to make a reaction at 70 degrees C. for six hours, the finely emulsified product was allowed to stand at 15 degrees C. for 12 hours to perform emulsion polymerization. Thereafter by using a 10% sodium carbonate water solution, the pH was adjusted to 6.0, and the polymerization was completed. The molecular weight of the polysiloxane obtained by the polymerization was 330,000, and the content of the vinyl group was 4.5 wt %. The prepared product was used as the component 1a.

(Component 1b)

75 g of polymethylhydrogensiloxane (content of the hydrogen group bonded to the silicon atom: 100 mol %, viscosity: 30 mPa·s, molecular weight: 2,100) having a trimethylsilyl group at both terminals thereof, 1.5 g of the dodecylbenzenesulfonic acid, and 73.5 g of water were measured and put in the 300 mL tall beaker. Thereafter by using the homo mixer, the mixture was stirred at the number of rotations of 6,000 rpm for 10 minutes to perform rough emulsification. After defoaming was performed under a decreased pressure, by using the pressure-type homogenizer, the mixture was fed to the pressure-type homogenizer twice under the condition of the pressure of 300 kg/cm$^2$ to perform fine emulsification. The prepared product was used as the component 1b.

(Component 2)

75 g of a polydimethylsiloxane solution (viscosity: 50 mPa·s, content of platinum: 3 wt %) consisting of a platinum-divinyltetramethyldisiloxane complex having the vinyl group at both terminals thereof, 7.5 g of ethynyl cyclohexanol, 1.5 g of the dodecylbenzenesulfonic acid, and 73.5 g of water were measured and put in the 300 mL tall beaker. Thereafter by using the homo mixer, the mixture was stirred at the number of rotations of 6,000 rpm for 10 minutes to perform rough emulsification. After defoaming was performed under a decreased pressure, the mixture was fed to the pressure-type homogenizer twice under the condition of the pressure of 300 kg/cm$^2$ to perform fine emulsification. The prepared product was used as the component 2.

(Component 3)

Methyltriethoxysilane, γ-ureidopropyltriethoxysilane, and γ-glycidoxypropyltrimethoxysilane were used as the component 3.

(Coating Solution)

100 g of the component 1a, 3.4 g of the component 1b, 0.17 g of the component 2, 1 g of the methyltriethoxysilane of the component 3, 1 g of the γ-ureidopropyltriethoxysilane, and 5 g of the γ-glycidoxypropyltrimethoxysilane, and 200 g of water were mixed with one another to prepare a coating solution.

Example 2

(Component 1a)

Except that the amount of the 1,3,5,7-tetravinyltetramethylcyclotetrasiloxane used in the example 1 was altered from 5 g to 10 g, a product was prepared in the same manner as that of the example 1. The prepared product was used as the component 1a. The molecular weight of the polysiloxane obtained by the polymerization was 310,000, and the content of the vinyl group was 5.4 wt %.

(Component 1b)

The product prepared in the same manner as that of the example 1 was used as the component 1b.

(Component 2)

The product prepared in the same manner as that of the example 1 was used as the component 2.

(Component 3)

Phenyltriethoxysilane, the γ-ureidopropyltriethoxysilane, and the γ-glycidoxypropyltrimethoxysilane were used as the component 3.

(Coating Solution)

100 g of the component 1a, 6.8 g of the component 1b, 0.34 g of the component 2, 1 g of the phenyltriethoxysilane of the component 3, 5 g of the γ-ureidopropyltriethoxysilane, and 5 g of the γ-glycidoxypropyltrimethoxysilane, and 200 g of water were mixed with one another to prepare a coating solution.

Example 3

(Component 1a)

Except that the amount of the 1,3,5,7-tetravinyltetramethylcyclotetrasiloxane used in the example 1 was altered from 5 g to 1 g, a product was prepared in the same manner as that of the example 1. The prepared product was used as the component 1a. The molecular weight of the polysiloxane obtained by the polymerization was 350,000, and the content of the vinyl group was 3.8 wt %.

(Component 1b)

The product prepared in the same manner as that of the example 1 was used as the component 1b.

(Component 2)

The product prepared in the same manner as that of the example 1 was used as the component 2.

(Component 3)

The phenyltriethoxysilane, the γ-ureidopropyltriethoxysilane, and the γ-glycidoxypropyltrimethoxysilane were used as the component 3.

(Coating Solution)

100 g of the component 1a, 0.68 g of the component 1b, 0.17 g of the component 2, 1 g of the phenyltriethoxysilane of the component 3, 5 g of the γ-ureidopropyltriethoxysilane, and 5 g of the γ-glycidoxypropyltrimethoxysilane, and 200 g of water were mixed with one another to prepare a coating solution.

Example 4

(Component 1a)
The product prepared in the same manner as that of the example 1 was used as the component 1a.
(Component 1b)
Except that the polymethylhydrogensiloxane (content of the hydrogen group bonded to the silicon atom: 100 mol %, viscosity: 30 mPa·s, molecular weight: 2,100) having the trimethylsilyl group at both terminals thereof was altered to a methylhydrogen siloxane-dimethylsiloxane copolymer (content of the hydrogen group bonded to the silicon atom: 30 mol %, viscosity: 35 mPa·s, molecular weight: 2,000) having the trimethylsilyl group at both terminals thereof, a product was prepared in the same manner as that of the example 1. The prepared product was used as the component 1b.
(Component 2)
The product prepared in the same manner as that of the example 1 was used as the component 2.
(Component 3)
The methyltriethoxysilane, the γ-ureidopropyltriethoxysilane, and the γ-glycidoxypropyltrimethoxysilane were used as the component 3.
(Coating Solution)
100 g of the component 1a, 11.2 g of the component 1b, 0.17 g of the component 2, 1 g of the methyltriethoxysilane of the component 3, 1 g of the γ-ureidopropyltriethoxysilane, and 5 g of the γ-glycidoxypropyltrimethoxysilane, and 200 g of water were mixed with one another to prepare a coating solution.

Example 5

(Component 1a)
The product prepared in the same manner as that of the example 1 was used as the component 1a.
(Component 1b)
The product prepared in the same manner as that of the example 1 was used as the component 1b.
(Component 2)
The product prepared in the same manner as that of the example 1 was used as the component 2.
(Component 3)
140 g of γ-aminopropyltriethoxysilane was dripped at a room temperature to a solution in which 62 g of maleic anhydride was dissolved in 200 g of ethanol. Thereafter a reaction was made for 15 hours while the ethanol was circulating at 80 degrees C. An obtained reactant, the methyltriethoxysilane, and the γ-glycidoxypropyltrimethoxysilane were used as the component 3.
(Coating Solution)
100 g of the component 1a, 3.4 g of the component 1b, 0.17 g of the component 2, 1 g of the methyltriethoxysilane of the component 3, 5 g of the reactant, 5 g of the γ-glycidoxypropyltrimethoxysilane, and 200 g of water were mixed with one another to prepare a coating solution.

Example 6

(Component 1a)
The product prepared in the same manner as that of the example 1 was used as the component 1a.

(Component 1b)
The product prepared in the same manner as that of the example 4 was used as the component 1b.
(Component 2)
The product prepared in the same manner as that of the example 1 was used as the component 2.
(Component 3)
The reactant obtained in preparing the component 3 of the example 5, the phenyltriethoxysilane, and the γ-glycidoxypropyltrimethoxysilane were used as the component 3.
(Coating Solution)
100 g of the component 1a, 11.2 g of the component 1b, 0.17 g of the component 2, 1 g of the phenyltriethoxysilane of the component 3, 5 g of the reactant, 5 g of the γ-glycidoxypropyltrimethoxysilane, and 200 g of water were mixed with one another to prepare the coating solution.

Example 7

(Component 1a)
125 g of polydimethylsiloxane (content of the vinyl group: 0.4 wt %, viscosity: 500 mPa·s, molecular weight: 17,200) having the vinyl group at both terminals thereof, 2.5 g of the dodecylbenzenesulfonic acid, and 122.5 g of water were measured and put in a 300 mL tall beaker. Thereafter by using the homo mixer, the mixture was stirred at 6,000 rpm for 10 minutes to perform rough emulsification. After defoaming was carried out under a decreased pressure, by using the pressure-type homogenizer, the mixture was fed to the pressure-type homogenizer twice under the condition of the pressure of 300 kg/cm$^2$ to perform fine emulsification. The prepared product was used as the component 1a.
(Component 1b)
The product prepared in the same manner as that of the example 1 was used as the component 1b.
(Component 2)
The product prepared in the same manner as that of the example 1 was used as the component 2.
(Component 3)
The methyltriethoxysilane, the γ-ureidopropyltriethoxysilane, and the γ-glycidoxypropyltrimethoxysilane were used as the component 3.
(Coating Solution)
100 g of the component 1a, 1 g of the component 1b, 0.17 g of the component 2, 1 g of the methyltriethoxysilane of the component 3, 5 g of the γ-ureidopropyltriethoxysilane, and 5 g of the γ-glycidoxypropyltrimethoxysilane, and 200 g of water were mixed with one another to prepare the coating solution.

Example 8

(Component 1a)
Except that the polydimethylsiloxane (content of the vinyl group: 0.4 wt %, viscosity: 500 mPa·s, molecular weight: 17,200) having the vinyl group at both terminals thereof was altered to the polydimethylsiloxane (content of the vinyl group: 0.04 wt %, viscosity: 10,000 mPa·s, molecular weight: 62,700) having the vinyl group at both terminals thereof, a product was prepared in the same manner as that of the example 7. The prepared product was used as the component 1a.
(Component 1b)
The product prepared in the same manner as that of the example 1 was used as the component 1b.

(Component 2)

The product prepared in the same manner as that of the example 1 was used as the component 2.

(Component 3)

The reactant obtained in preparing the component 3 of the example 5, the methyltriethoxysilane, and the γ-glycidoxypropyltrimethoxysilane were used as the component 3.

(Coating Solution)

100 g of the component 1a, 0.2 g of the component 1b, 0.34 g of the component 2, 1 g of the methyltriethoxysilane of the component 3, 5 g of the reactant, 5 g of the γ-glycidoxypropyltrimethoxysilane, and 200 g of water were mixed with one another to prepare the coating solution.

Comparison Example 1

(Component 1a)

125 g of the octamethylcyclotetrasiloxane, 2.5 g of the dodecylbenzenesulfonic acid, and 22.5 g of water were measured and put in a 300 mL tall beaker. Thereafter by using the homo mixer, the mixture was stirred at the number of rotations of 6,000 rpm for 10 minutes. Thereafter 100 g of water was gradually added to the mixture at the number of rotations of 2,000 rpm to perform rough emulsification. After defoaming was performed under a decreased pressure, the mixture was fed to the pressure-type homogenizer twice under the condition of the pressure of 300 kg/cm$^2$ to perform fine emulsification. After a finely emulsified product was allowed to make a reaction at 70 degrees C. for six hours, the finely emulsified product was allowed to stand at 15 degrees C. for 12 hours to perform emulsion polymerization. Thereafter by using the 10% sodium carbonate water solution, the pH was adjusted to 6.0, and the polymerization was completed. The molecular weight of the polysiloxane having the silanol group at both terminals thereof was 330,000. The prepared product was used as the component 1a.

(Component 1b)

The component 1b was not used in the comparison example 1.

(Component 2)

75 g of dioctyl tin dilaurate, 12.5 g of polyoxyethylene styrenated phenyl ether diethylene, and 162.5 g of water were measured and put in the 300 mL tall beaker. Thereafter by using the homo mixer, the mixture was stirred at the number of rotations of 6,000 rpm for 10 minutes to perform rough emulsification. After defoaming was performed under a decreased pressure, the mixture was fed to the pressure-type homogenizer twice under the condition of the pressure of 300 kg/cm$^2$ to perform fine emulsification. The prepared product was used as the component 2. The reaction inhibitor used in the examples was not used.

(Component 3)

The methyltriethoxysilane, the γ-ureidopropyltriethoxysilane, and the γ-glycidoxypropyltrimethoxysilane were used as the component 3.

(Coating Solution)

100 g of the component 1a, 1 g of the component 2, 1 g of the methyltriethoxysilane of the component 3, 1 g of the γ-ureidopropyltriethoxysilane, and 5 g of the γ-glycidoxypropyltrimethoxysilane, and 200 g of water were mixed with one another to prepare the coating solution.

The core parts, of gaskets for syringes, having the configuration shown in FIGS. 1 and 2 were made by using butyl rubber. The core parts were formed by press-molding a vulcanizable rubber composition composed of butyl rubber to which an additive was added. Regarding the configuration of the obtained core parts, the length of every core part was 20 mm; the outer diameter of the core part at the distal-side and proximal-side annular ribs thereof was 30 mm; the length between the center of the distal-side annular rib and that of the proximal-side annular rib was 10 mm; the outer diameter of the core part at an equal-diameter portion thereof between the distal-side and proximal-side annular ribs was 27 mm; the length (depth) of the plunger-mounting portion of the core part having a female screw at the inner side thereof was 10 mm; and the inner diameter of a concave portion for connecting the plunger at its distal side and proximal side were 18 mm and 21 mm respectively. After the core members of the gaskets made as described above at a room temperature and in a normal pressure were heat-treated at 90 degrees C. for 30 minutes, the gaskets were rotated (300 rpm) on the respective axis thereof, and the coating solutions of the examples 1 through 8 and the comparison example 1 were sprayed to the gaskets respectively from the respective side surface thereof. Thereafter the gaskets were dried at 150 degrees C. for 30 minutes. In this manner, the gaskets were made. Thereafter to wash an extra coating liquid present on the gaskets, cleaning was performed with purified water having a temperature not less than 80 degrees C. The average thickness of the coating layer formed on the surface of each core member was about 10 μm.

Experimental Examples

Experiment 1

Sliding Resistance Measurement Test

Polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1 through 8 and the comparison example 1, and the above-described plungers were assembled to form the syringes. The sliding resistance value of each syringe was measured by using an autograph (model name: EZ-Test, manufactured by Shimazu Seisakusho Co., Ltd.). With the distal end of each syringe and the proximal end of the plunger being fixed to a fixing portion of the autograph to which an object to be measured is fixed, the plungers were moved downward 60 mm at a speed of 100 mm/minute to measure the initial sliding resistance value and maximum sliding resistance value (N) of each syringe. Table 1 shows the results.

As shown in table 1, the syringes using the gaskets of examples 1 through 8 and comparison example 1 had comparable initial and maximum sliding resistance values. In addition, each of the syringes had a small difference between the initial sliding resistance value and maximum sliding resistance value thereof. There is little fear that more than a predetermined amount of a medical agent solution is discharged from the syringes when the plungers were started to be pressed. Therefore the syringes were capable of discharging the medical agent solution safely and accurately. Favorable results that the initial and maximum sliding resistance values were not more than 10N were obtained.

TABLE 1

|  | Sliding resistance value (N) | | | High-penetration liquid sealing |
| --- | --- | --- | --- | --- |
|  | Initial | Maximum | Pressure test | performance test |
| Example 1 | 5.1 | 7.1 | Passed | Passed |
| Example 2 | 5.9 | 7.3 | Passed | Passed |
| Example 3 | 5.5 | 7.0 | Passed | Passed |
| Example 4 | 5.3 | 7.1 | Passed | Passed |
| Example 5 | 5.2 | 7.2 | Passed | Passed |
| Example 6 | 4.8 | 6.9 | Passed | Passed |
| Example 7 | 6.8 | 8.3 | Passed | Passed |
| Example 8 | 7.1 | 8.5 | Passed | Passed |
| Comparison example 1 | 5.2 | 7.3 | Passed | Passed |

The above-described outer cylinders for the syringes, the gaskets of example 1 through 8 and comparison example 1, and the above-described plungers were assembled to form the syringes. Thereafter 40 ml of purified water was injected to each syringe barrel. After a sealing member was fitted on the distal end of each syringe barrel to seal it, autoclave sterilization was performed. Thereafter the sliding resistance value of each syringe was measured by the autograph (model name: EZ-Test, manufactured by Shimazu Seisakusho Co., Ltd.) in the above-described manner. The initial sliding resistance value of each syringe and the maximum sliding resistance value (N) thereof were measured at a test speed of 20 to 500 mm/minute. Table 2 shows the results.

As shown in table 2, it has been found that the syringes using the gaskets of example 1 through 8 and the syringe using the gasket of comparison example 1 had similar sliding resistance values and had low sliding resistance values at a test speed lower than 100 mm/minute. Thus it has been found that at a speed suitable for injecting the medical agent into a vein, the syringes using the gaskets of example 1 through 8 had good sliding performance.

The number of samples used in each test was 10. The numerical values in the tables show the average of the values of the 10 samples.

TABLE 2

|  | Maximum sliding resistance value (N) | | | | | |
| --- | --- | --- | --- | --- | --- | --- |
|  | 20 mm/min | 30 mm/min | 50 mm/min | 100 mm/min | 200 mm/min | 500 mm/min |
| Example 1 | 9.6 | 10.4 | 11.1 | 15.0 | 20.9 | 29.0 |
| Example 2 | 9.2 | 10.0 | 10.9 | 14.8 | 20.5 | 28.9 |
| Example 3 | 9.4 | 10.5 | 11.2 | 15.1 | 20.6 | 29.3 |
| Example 4 | 9.2 | 10.2 | 11.5 | 14.9 | 20.2 | 29.0 |
| Example 5 | 9.3 | 10.7 | 11.0 | 14.6 | 20.8 | 28.8 |
| Example 6 | 9.5 | 10.4 | 11.5 | 15.5 | 20.1 | 29.5 |
| Example 7 | 9.9 | 11.9 | 12.5 | 15.6 | 19.2 | 23.9 |
| Example 8 | 9.8 | 11.7 | 12.6 | 15.8 | 20.8 | 25.3 |
| Comparison example 1 | 9.5 | 10.2 | 11.5 | 15.5 | 21.3 | 29.2 |

By using glass (produced by Shiotani Glass Co., Ltd.) as a material of outer cylinders for syringes, the outer cylinders for the syringes having the configuration shown in FIG. 5 were formed. The cylindrical portion of each of the outer cylinders for the syringes had an inner diameter of 23 mm and a length of 76 mm. The polypropylene (produced by Japan Polychem Corporation) used as a material forming plungers was injection-molded to form the plungers each having the configuration shown in FIG. 5.

The above-described outer cylinders for the syringes, the gaskets of example 1 through 8 and comparison example 1, and the above-described plungers were assembled to form syringes. Thereafter 20 ml of purified water was injected to the outer cylinders. Thereafter sliding resistance values were measured by the autograph (model name: EZ-Test, manufactured by Shimazu Seisakusho Co., Ltd.) in the above-described manner. With the distal end of each syringe and the proximal end of each plunger being fixed to the fixing portion of the autograph to which an object to be measured is fixed, each plunger was moved downward 45 mm at speeds of 20, 50, 100, and 500 mm/minute to measure the maximum sliding resistance value (N). Table 3 shows the results.

TABLE 3

|  | Maximum sliding resistance value (N) | | | |
| --- | --- | --- | --- | --- |
|  | 20 mm/min | 50 mm/min | 100 mm/min | 500 mm/min |
| Example 1 | 6.1 | 7.2 | 11.2 | 14.1 |
| Example 2 | 6.2 | 7.4 | 11.3 | 14.3 |
| Example 3 | 6.0 | 7.1 | 11.2 | 14.0 |
| Example 4 | 6.4 | 7.3 | 11.5 | 14.6 |
| Example 5 | 6.3 | 7.2 | 11.3 | 14.2 |
| Example 6 | 6.1 | 7.0 | 11.2 | 14.1 |
| Example 7 | 6.8 | 7.9 | 12.0 | 14.9 |
| Example 8 | 7.0 | 8.0 | 12.4 | 15.0 |
| Comparison example 1 | 6.0 | 7.3 | 11.4 | 14.2 |

Experiment 2

Pressure Test Specified in Standard of Sterilized Syringe Barrel

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of examples 1 through 8 and comparison example 1, and the above-described plungers were assembled to form the syringes.

A test was conducted in accordance with the pressure test specified in the standard of the sterilized plastic syringe barrel which can be immediately used as it is and disposed after using it one time (notified on Dec. 11, 1998 by Director of Pharmaceutical and Medical Safety Bureau in No. 1079 issue of Pharmaceutical Development). Table 1 shows the results.

The number of samples used in the test was five. "Passed" was indicated for samples of the examples and the comparison example in which all of the five samples passed inspection.

Experiment 3

Test for Examining Sealing performance of High-Penetration Liquid

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of the examples 1 through 8 and the comparison example 1, and the above-described plungers were assembled to form the syringes. Thereafter by using an "Ageless"™ "Checker" (produced by Mitsubishi Gas Chemical Company) for use in a test for examining the sealing performance of a heat sealing portion made of a soft plastic packing material, a sealing performance test (the distal end of the syringe was sealed in the length of 40 ml by fitting the sealing member on the distal end thereof) was conducted. The syringes were left overnight to visually observe liquid leak from the sliding portion of each gasket. Table 1 shows the results.

The number of samples used in the test was five. "Passed" was marked for the samples of the examples and the comparison example in which all of the five samples passed inspection.

Experiment 4

Fixing Test

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material of plungers was injection-molded to form the plungers each having the configuration shown in FIG. 5.

The above-described outer cylinders for the syringes, the gaskets of examples 1 and 7 and comparison example 1, and the above-described plungers were assembled to form syringes. Thereafter the syringes were allowed to stand one day in a constant-temperature bath having temperatures of 40 degrees C., 60 degrees C., and 80 degrees C. and thereafter 10 days, 20 days, and 30 days in the constant-temperature bath having a temperature of 60 degrees C. To evaluate the fixing degree of each gasket to the outer cylinder for the syringe, the initial sliding resistance value of each syringe was measured by the autograph (model name: EZ-Test, manufactured by Shimazu Seisakusho Co., Ltd.). With the distal end of each syringe and the proximal end of each plunger being fixed to the fixing portion of the autograph to which an object to be measured is fixed, the plungers were moved downward 60 mm at a speed of 100 mm/minute to measure the initial sliding resistance value (N) of each syringe. Table 4 shows the results.

TABLE 4

| | Initial sliding resistance value (N) | | | | | | |
|---|---|---|---|---|---|---|---|
| | Initial time point in test | 40 degrees C. | 60 degrees C. one day | 80 degrees C. | 60 degrees C. | | |
| | | | | | 10 days | 20 days | 30 days |
| Example 1 | 4.96 | 5.49 | 6.12 | 7.36 | 7.52 | 6.95 | 8.90 |
| Example 7 | 5.39 | 5.39 | 5.76 | 6.12 | 6.33 | 6.44 | 7.32 |
| Comparison example 1 | 4.99 | 5.46 | 6.14 | 7.39 | 7.54 | 6.94 | 8.93 |

Experiment 5

Test for Examining Insoluble Fine Particles

The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material forming plungers was injection-molded to form the plungers each having the configuration shown in FIG. 5. The above-described outer cylinders for the syringes, the gaskets of the examples 1 and 7 and the comparison example 1, and the above-described plungers were assembled to form syringes. Thereafter 40 ml of purified water was injected to each syringe barrel. After the sealing member was fitted on the distal end of the syringe barrel to seal it, autoclave sterilization was performed to produce prefilled syringes. Thereafter the number of insoluble fine particles in the purified water was measured after the syringes were violently vibrated for 10 minutes. Table 5 shows the results.

TABLE 5

| | Number (piece) of insoluble fine particles per syringe | | |
|---|---|---|---|
| | Not less than 5 μm | Not less than 10 μm | Not less than 25 μm |
| Example 1 | 33 | 3 | 0 |
| Example 7 | 36 | 6 | 0 |
| Comparison example 1 | 34 | 4 | 0 |

Experiment 6

Flow Rate Accuracy Evaluation Test Conducted by Using Syringe Pump

By using a syringe pump (TE-331 produced by Terumo Corporation), the flow rate accuracy of each syringe was evaluated. The polypropylene (produced by Japan Polychem Corporation) used as a material forming outer cylinders for syringes was injection-molded to form the outer cylinders for the syringes each having the configuration shown in FIG. 5. The cylindrical portion of each of the outer cylinders for the syringes had an inner diameter of 29 mm and a length of 121 mm. The polypropylene (produced by Japan Polychem Corporation) used as a material forming plungers was injection-molded to form the plungers each having the configuration shown in FIG. 5.

The above-described outer cylinders for the syringes, the gaskets of examples 1 and 7 and comparison example 1, and the above-described plungers were assembled to form syringes. Thereafter 40 ml of purified water was injected to each syringe barrel. After the sealing member was fitted on the distal end of the syringe barrel to seal it, autoclave sterilization was performed. Thereafter each syringe was set on the syringe pump to discharge the purified water for eight hours at a flow rate of 5 ml/hour. By using an electronic balance, the weight of the discharged purified water was measured at intervals of 30 seconds. As a result, it has been confirmed that the gaskets of examples 1 and 7 and comparison example 1 stably discharged the purified water.

Industrial Applicability

An exemplary medical appliance having a slidable coating layer is as described below.

(1) The medical appliance having a slidable coating layer can move in contact with an inner surface of a medical member or that of a lumen and can have a slidable coating layer formed at a part thereof which contacts the medical member or the lumen. The slidable coating layer can be formed of a composition which does not contain solid fine particles and contains a silicone-based resin which is a product of an addition reaction between silicone having a vinyl group and silicone having a hydrogen group bonded to a silicon atom.

Exemplary embodiments may have the following forms:

(2) The medical appliance having a slidable coating layer according to the above (1), wherein the silicone having the vinyl group is prepared by an emulsion polymerization method.

(3) The medical appliance having a slidable coating layer according to the above (1), wherein the silicone having the vinyl group is prepared by a dispersion emulsification method.

(4) The medical appliance having a slidable coating layer according to any one of the above (1) through (3), wherein the composition does not contain a tin-based compound.

(5) The medical appliance having a slidable coating layer according to any one of the above (1) through (4), wherein the composition contains a platinum group metal-based catalyst.

(6) The medical appliance having a slidable coating layer according to any one of the above (1) through (5), wherein the silicone-based resin of the composition is formed by hydrosilylation between the vinyl group of the silicone and silicon bonded to the hydrogen group, of the silicone, bonded to the silicon atom.

(7) The medical appliance having a slidable coating layer according to any one of the above (1) through (6), wherein the silicone having the hydrogen group bonded to the silicon atom is a homopolymer or a copolymer of polymethylhydrosiloxane having a trimethylsilyl group at both terminals thereof.

(8) The medical appliance having a slidable coating layer according to any one of the above (1) through (7), wherein the silicone having the hydrogen group bonded to the silicon atom is a homopolymer or a copolymer of polydimethylsiloxane having the hydrogen group bonded to the silicon atom at both terminals thereof.

(9) The medical appliance having a slidable coating layer according to any one of the above (1) through (8), wherein the silicone having the vinyl group is siloxane or silane having the vinyl group.

(10) The medical appliance having a slidable coating layer according to any one of the above (1) through (9), wherein the composition contains alkyl alkoxy silane or phenylalkoxysilane and in addition, glycidoxy alkyl alkoxysilane.

(11) The medical appliance having a slidable coating layer according to any one of the above (1) through (10), wherein the composition contains alkoxysilane having an ureido group or an uraren group or/and a product formed by a reaction between alkoxysilane having an amino group and a carboxylic anhydride.

(12) The medical appliance having a slidable coating layer according to any one of the above (1) through (11), wherein the silicone-based resin is a thermosetting silicone-based resin.

(13) The medical appliance having a slidable coating layer according to any one of the above (1) through (12), wherein the coating layer has a thickness of 1 to 30 µm.

(14) The medical appliance having a slidable coating layer according to the above (13), wherein an initial sliding resistance value of the coating layer is not more than a maximum value of a dynamic sliding resistance value thereof.

(15) The medical appliance having a slidable coating layer according to any one of the above (1) through (14), wherein the medical appliance is a guide wire or a catheter.

(16) The medical appliance having a slidable coating layer according to any one of the above (1) through (15), wherein the medical member is an outer cylinder for a syringe; the medical appliance is a gasket for the syringe slidably accommodated inside the outer cylinder for the syringe; and the gasket has a gasket body made of an elastic body and the slidable coating layer formed on a part thereof which contacts at least the outer cylinder for the syringe.

(17) The medical appliance having a slidable coating layer according to the above (16), wherein the medical member is a plastic outer cylinder for a syringe; and the medical appliance is a gasket for the plastic outer cylinder for the syringe.

An exemplary syringe is as described below:

(18) A syringe includes an outer cylinder for the syringe; a gasket, for the syringe, which is a medical appliance having a slidable coating layer, according to claim 16 or 17, slidably accommodated inside the outer cylinder; and a plunger which is mounted or can be mounted on the gasket.

(19) The syringe according to the above (18), wherein a medical agent solution is filled.

(20) The syringe according to the above (18) or (19), wherein a dynamic sliding resistance value of the gasket is not more than 20N when the gasket slides inside the outer cylinder at a low speed (100 mm/minute).

(21) The syringe according to any one of the above (18) and (20), wherein the outer cylinder is made of plastics.

It will be appreciated by those skilled in the art that the presently disclosed embodiments are therefore considered in all respects to be illustrative and not restricted.

What is claimed is:

1. A coated medical appliance, comprising:
   a medical appliance which is configured to move while being in contact with an inner surface of a medical member or an inner surface of a lumen; and
   a slidable coating layer, wherein the slidable coating layer is formed at a part of the medical appliance for contacting said medical member or said lumen,
   wherein said slidable coating layer is formed of a composition which does not contain solid fine particles,
   wherein said slidable coating layer contains a silicone-based resin which is a product of an addition reaction between silicone having a vinyl group and silicone having a hydrogen group bonded to a silicon atom.

2. The coated medical appliance according to claim 1, wherein said silicone having said vinyl group is prepared by an emulsion polymerization method.

3. The coated medical appliance according to claim 1, wherein said silicone having said vinyl group is prepared by a dispersion emulsification method.

4. The coated medical appliance according to claim 1, wherein said composition does not contain a tin-based compound.

5. The coated medical appliance according to claim 1, wherein said composition contains a platinum group metal-based catalyst.

6. The coated medical appliance according to claim 1, wherein said silicone-based resin of said composition is formed by hydrosilylation between said vinyl group of said silicone and silicon bonded to said hydrogen group, of said silicone, bonded to said silicon atom.

7. The coated medical appliance according to claim 1, wherein said silicone having said hydrogen group bonded to said silicon atom is a homopolymer or a copolymer of polymethylhydrosiloxane having a trimethylsilyl group at both terminals thereof.

8. The coated medical appliance according to claim 1, wherein said silicone having said hydrogen group bonded to said silicon atom is a homopolymer or a copolymer of polydimethylsiloxane having said hydrogen group bonded to said silicon atom at both terminals thereof.

9. The coated medical appliance according to claim 1, wherein said silicone having said vinyl group is a siloxane or a silane having said vinyl group.

10. The coated medical appliance according to claim 1, wherein said composition contains an alkyl alkoxy silane or a phenylalkoxysilane and in addition, a glycidoxy alkyl alkoxysilane.

11. The coated medical appliance according to claim 1, wherein said composition contains an alkoxysilane having an ureido group, an uraren group, a product formed by a reaction between an alkoxysilane having an amino group and a carboxylic anhydride, or a combination thereof.

12. The coated medical appliance according to claim 1, wherein said silicone-based resin is a thermosetting silicone-based resin.

13. The coated medical appliance according to claim 1, wherein said slidable coating layer has a thickness of 1 to 30 μm.

14. The coated medical appliance according to claim 13, wherein an initial sliding resistance value of said slidable coating layer is not more than a maximum value of a dynamic sliding resistance value thereof.

15. The coated medical appliance according to claim 1, wherein said medical appliance is a guide wire or a catheter.

16. The coated medical appliance according to claim 1, wherein said medical member is an outer cylinder for a syringe; said medical appliance is a gasket for said syringe slidably accommodated inside said outer cylinder for said syringe; and said gasket has a gasket body made of an elastic body and said slidable coating layer formed on a part thereof which contacts at least said outer cylinder for said syringe.

17. The coated medical appliance according to claim 16, wherein said medical member is a plastic outer cylinder for a syringe; and said medical appliance is a gasket for said plastic outer cylinder for said syringe.

18. A syringe, comprising:
an outer cylinder; and
the coated medical appliance according to claim 1, wherein the coated medical appliance is a gasket slidably accommodated inside said outer cylinder; and
a plunger which is mounted or capable of being mounted on said gasket.

19. The syringe according to claim 18, wherein the syringe contains a medical agent solution.

20. The syringe according to claim 18, wherein a dynamic sliding resistance value of said gasket is not more than 20 N when said gasket slides inside said outer cylinder at a low speed (100 mm/minute).

21. The syringe according to claim 18, wherein said outer cylinder is made of a plastic.

22. The syringe according to claim 18, wherein the gasket comprises a gasket body made of an elastic body, and wherein the slidable coating layer is formed on a part of the gasket which contacts at least said outer cylinder.

23. The coated medical appliance according to claim 1, wherein the medical appliance is a gasket for a syringe, a catheter, a guide wire, or a blood vessel dilation appliance.

* * * * *